US007629115B2

(12) United States Patent
Gu et al.

(10) Patent No.: US 7,629,115 B2
(45) Date of Patent: Dec. 8, 2009

(54) CELL-BASED PLATFORM FOR HIGH THROUGHPUT SCREENING

(75) Inventors: Yuandong Gu, Plymouth, MN (US); Leon Xu, Shanghai (CN); Jicang Zhou, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 975 days.

(21) Appl. No.: 11/129,074

(22) Filed: May 13, 2005

(65) Prior Publication Data

US 2006/0286661 A1 Dec. 21, 2006

(51) Int. Cl.
*C12Q 1/00* (2006.01)

(52) U.S. Cl. .......................................................... 435/4

(58) Field of Classification Search ...................... 435/4
See application file for complete search history.

(56) References Cited

U.S. PATENT DOCUMENTS

| | | | | |
|---|---|---|---|---|
| 3,929,583 | A * | 12/1975 | Sharpe et al. | 435/288.5 |
| 5,976,813 | A | 11/1999 | Beutel et al. | |
| 6,017,767 | A * | 1/2000 | Chandler | 436/514 |
| 6,565,813 | B1 | 5/2003 | Garyantes | |
| 2003/0098121 | A1* | 5/2003 | Moya | 156/275.1 |

FOREIGN PATENT DOCUMENTS

| | | | |
|---|---|---|---|
| DE | 2655977 | | 6/1978 |
| EP | 0576753 | A1 | 1/1994 |
| WO | WO-0164344 | A2 | 9/2001 |
| WO | WO 01/64344 | * | 10/2001 |
| WO | WO-0245858 | A2 | 6/2002 |
| WO | WO-2004068107 | A2 | 8/2004 |
| WO | WO-2005103691 | A1 | 11/2005 |

OTHER PUBLICATIONS

J. Ziauddin and D. Sabatini: "*Microarrays of cells expressing defined cDNA's*", Nature, vol. 411 (May 3, 2001) (pp. 107-110).

S. Bailey, et al.: "*Applications of transfected cell microarrays in high-throughput drug discovery*" Drug Discovery Today Vo. 7, No. 18 (2002) (high-throughput technologies. Supplement/reviews (pp. S113-S118).

* cited by examiner

*Primary Examiner*—Walter D Griffin
*Assistant Examiner*—Lydia Edwards
(74) *Attorney, Agent, or Firm*—Kris T. Fredrick

(57) ABSTRACT

The present invention relates to an apparatus for testing multiple sample compounds for their biological effect comprising a porous block having substantially planar top and bottom surfaces. The top surface comprises a plurality of cell adhesive regions and cell dis-adhesive regions and the bottom surface provides multiple sites to load the sample compounds. These sites are located opposite from the cell adhesive regions on the top surface of the porous block. In certain embodiments, the invention further comprises at least one dissolvable layer which provides multiple sites to load the sample compounds.

39 Claims, 5 Drawing Sheets

CELL-BASED PLATFORM FOR HIGH THROUGHPUT SCREENING

FIELD OF THE INVENTION

High throughput screening technology was developed in part to address the problem of screening large populations of compounds for biological activity in the pharmaceutical industry. Using microarray techniques and a variety of specialized assays, large numbers of compounds are tested in parallel and under identical conditions to determine whether they possess useful biological activity. Assays that measure biological activity in living cells require incubating the cells with thousands of different drug candidates. This incubation is traditionally accomplished in multi-well titer plates in standardized 96, 384, and 1536 well configurations. The multi-well plates are used in conjunction with automated fluid dispensing systems and standardized assays to rapidly screen the sample compounds.

SUMMARY OF THE INVENTION

The present invention relates, in one aspect, to an apparatus for testing multiple sample compounds for their biological effect comprising a porous block having substantially planar top and bottom surfaces. The top surface comprises a plurality of cell adhesive regions and cell dis-adhesive regions and the bottom surface provides multiple sites to load the sample compounds. These sites are located opposite from the cell adhesive regions on the top surface of the porous block.

In another aspect, the present invention relates to an apparatus as described above, but further comprising at least one dissolvable layer which provides multiple sites to load the sample compounds. These sites are located opposite from the cell adhesive regions on the top surface of the porous block.

In certain embodiments, the apparati described above further comprise a frame surrounding the porous block. In other embodiments the apparati described above further comprise a wall that rises above and surrounds the top surface. The combination of the wall and the top surface is capable of retaining a liquid.

DETAILED DESCRIPTION OF THE INVENTION

The present invention relates to various types of apparatus for testing multiple sample compounds for their biological effect. These apparati are used to determine whether a given test compound affects the biological activity of a cell. A biological effect is any measurable change in or on a cell. Such changes include, but are not limited to, changes in cell appearance or structure, changes in cell activity, changes in gene expression levels, changes in cell protein expression levels, changes in cell protein activity, and changes in cell protein stability.

Existing 96- and 384-well plates are limited in their ability to rapidly and efficiently screen large numbers of associated compounds with cell-lines of interest. Moreover, the four-fold processing improvement when moving to 1536-well plates is offset by significant fluid handling problems. Working volumes for the 1536-well format are typically below 10 microliters. At such low volumes, chemical volatility, solvent evaporation, and gas bubbles will contribute to large inter-sample statistical variations. These problems are aggravated by a high-variance cell number distribution corresponding to individual well cell populations which result in high inter-well dose variation. These physical limitations contribute to high statistical variations in subsequent assay measurements, undermining precision and reliability.

The apparatus and methods of the present invention solve many of the fluid handling problems associated with high-density multi-well screening methods by foregoing the multi-well format and instead using a porous matrix as both a locus for drug candidate deposition and a support for cells and other assay reagents. Surface characteristics engineered on both sides of the porous matrix block aid in localizing the interaction of assay reagents with the sample and confining visualization areas to pre-determined regions on the surface cell side of the porous block.

Figure 1:
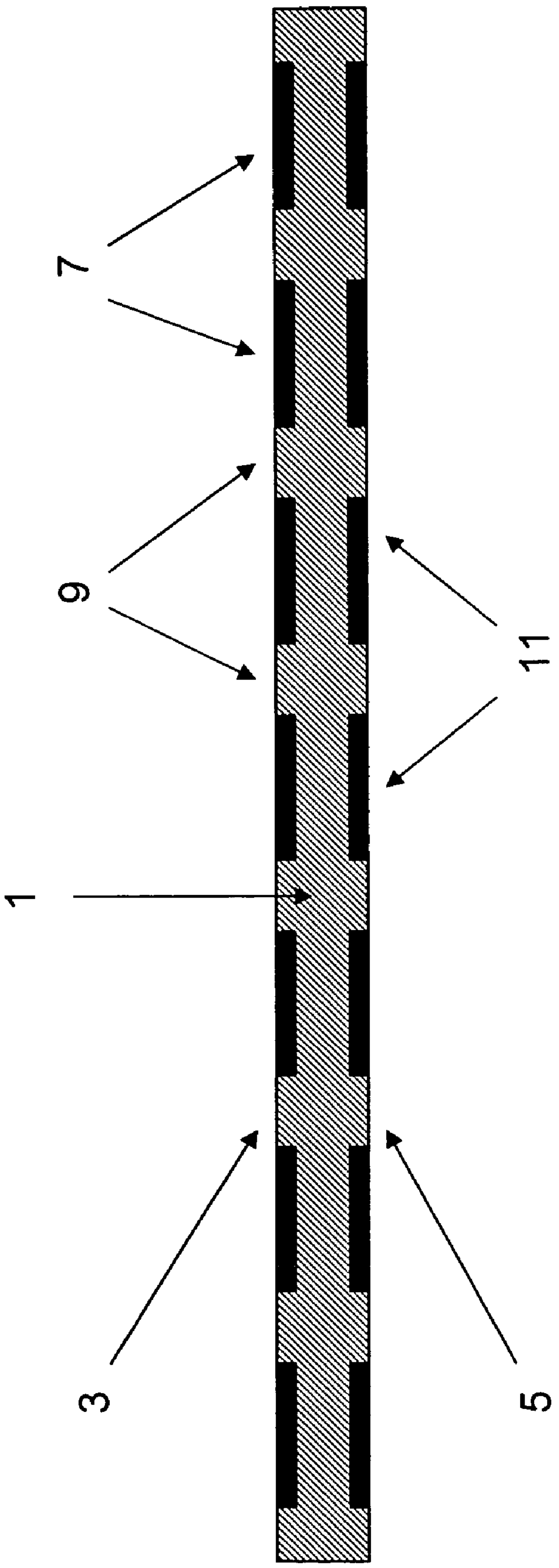
FIG. 1. Cross sectional view of apparatus with multiple hydrophilic sites (11) to load the sample compounds, located opposite from hydrophilic cell adhesive regions (7).

An apparatus of the present invention includes, as illustrated in FIG. 1, a porous block (1) having substantially planar top (3) and bottom surfaces (5). The top surface comprises a plurality of cell adhesive regions (7) and cell dis-adhesive regions (9), and the bottom surface incorporates multiple sites (11) to load the sample compounds. These sites (11) are located opposite from the cell adhesive regions. Sample compounds are deposited onto the surface of the bottom of the porous matrix within site (11) designed to attract and absorb the compound into the porous matrix. After absorption, cells are spread onto the top surface of the porous block. The cells adhere to the top surface after incubation in the incubator. Sample compounds diffuse through the porous matrix to its top surface and interact with cells which are fixed to the top surface. The methods of the present invention allow the assay surface (top) (3) to be prepared after samples have been deposited onto the bottom surface (5).

A description of the various components of the apparatus of the present invention follows below.

The porous block may be made of any material so long as it is permeable to the compounds to be tested. The porous block may comprise a polymer, gel, or membrane as described below.

In one embodiment the porous block is made of a polymer compound. Suitable polymers are polyamide, poly(ethylene-co-vinyl acetate) (EVAc), polystyrene, polypropylene, polycarbonate, polyester, polyethylene, polyvinylidene, polymethylmethacrylate, and polyethylene terapthalate. In preferred embodiments, the polymer layer is transparent or semi-transparent to aid in the optical observation. The polymer layer is fabricated using conventional polymer molding techniques such as hot embossing, injection molding, extension molding, and methods known in the art.

In preferred embodiments the polymer is a polyamide or EVAc. In particularly preferred embodiments the polymer is nylon.

In other embodiments the porous block is in the form of a gel. Examples of such gels includes gelatin, agarose, and acrylamide gels. Agarose and polyacrylamide gels are physically or chemically cross-linked, spongelike structures. Although they may contain up to 99.5% water, the size of the pores of these gels is similar to that of many proteins and nucleic acids. Gels are tailored to sieve molecules of a wide range of sizes by appropriate choice of matrix concentration. The average pore size of a gel is determined by the percentage of solids in the gel and, for polyacrylamide, by the amount of cross-linker as well. In preferred embodiments the gel is agarose, gelatin, α-Hydro-ω-hydroxypoly(oxyethylene)poly (oxypropylene)poly(oxyethylene) block copolymer, and stimuli sensitive hydrogel, and modified starch/cellulose. In particularly preferred embodiments the gel is made of cellulose derivatives. In another preferred embodiment the gel is stimuli sensitive hydrogel. In another particularly preferred embodiment the stimuli sensitive hydrogel is selected from the group consisting of poly(n-isopropylarylamide) and polyacrylic acid.

In yet another embodiment the porous block is a membrane. In preferred embodiments the membrane is nylon, cellulose, EVAc, PET, or polysulfone. In particularly preferred embodiments the membrane is nylon with particular pore size that will allow the sample compounds to diffuse or pass through the membrane.

The cell adhesive region of the top surface of the porous block is a region to which cells can bind or adhere. The top surface of the porous block may inherently comprise cell adhesive regions or the top surface of the porous block may be modified to form cell adhesive regions. Cell adhesive regions are designed to allow cells to associate or adhere to the top surface. A variety of methods may be used to prepare the cell adhesive regions. Examples of such methods include hydrophilization of the cell adhesive regions. Methods of hydrophilization include attachment of synthetic polymers, attachment of proteins, chemical modification, photochemical modification, modification with reactive plasma, and physical modification. Each of these methods of preparation of cell adhesive regions is discussed in detail below.

In certain embodiments the top surface is modified by regional hydrophilization to form the cell adhesive regions. Hydrophilization refers to modifying or using a surface which is “water-loving”, that is, a region which contains charged or polar molecules. In a preferred embodiment the top surface is modified by regional addition of at least one peptide to form the cell adhesive regions.

In certain embodiments a surface is made hydrophilic by use of synthetic polymers. In particular, the surface is regionally coated with a layer of polymer to facilitate the cell adhesion, such as polystyrene, polytetrafluoroethylene, polycarbonate and polyethylene terephthalate. This synthetic polymeric coating creates a uniform net positive charge on the plastic surface which, for some cell types, can enhance cell attachment, growth and differentiation, especially in serum-free and low serum conditions. Poly-D-lysine surfaces often improve attachment and growth of primary neurons, glial cells, neuroblastomas, and a variety of transfected cell lines, including HEK-293. In preferred embodiments of the present invention, a cell adhesion motif is grafted onto the top surface of the porous matrix within the regions defined by differing wettabilities. Cell adhesion motifs improve the formation of a uniform cell monolayer on the surface and additionally, allow a biologically realistic interaction of sample compounds with the adhered cells.

In a preferred embodiment the top surface is modified by the regional addition of at least one peptide or protein to form the cell adhesive regions.

The RGD (arginine-glycine-aspartic acid; SEQ ID NO: 1) sequence is found in several important extracellular matrix proteins and serves as an adhesion ligand for members of the integrin family of cell-surface receptors. A typical RGD sequence is Gly-Arg-Gly-Asp-Ser-Pro (GRGDSP; SEQ ID NO: 2). Cyclic RGD may also be used as a cell adhesion motif. A typical sequence is Arg-Gly-Asp-(D-Phe)-Val (SEQ ID NO: 3). The RGD modified surface directs the formation of a cell monolayer in situ on the membrane.

Integrins are a large family of heterodimeric transmembrane glycoproteins that attach cells to extracellular matrix proteins of the basement membrane or to ligands on other cells. Integrins contain large (a) and small (β) subunits of sizes 120-170 kDa and 90-100 kDa, respectively. Some integrins mediate direct cell to cell recognition and interactions. Integrins contain binding sites for divalent cations $Mg^{2+}$ and $Ca^{2+}$, which are necessary for their adhesive function. Mammalian integrins form several subfamilies sharing common β subunits that associate with different α subunits. β2 integrins are exclusively expressed on leukocytes and undergo a conformational change encompassing the phosphorylation of the β subunit upon activation. However, this phosphorylation is neither necessary nor sufficient for conformational activation. The activation status is controlled by the Gly-Phe-Phe-Lys-Arg (GFFKR; SEQ ID NO: 4) site immediately adjacent to the transmembrane domain of the alpha chain.

In certain embodiments, the surface is modified or absorbed with glycoprotein, such as fibronectin, lamnin, vitronecin, collagen and to facilitate cell adhesion. They are components of the extracellular matrix and interact with integrins. In other embodiments, the surface is modified by regional saccharification.

In another preferred embodiment, the top surface is modified by chemical groups to form the cell adhesive regions. In a particularly preferred embodiment, the chemical groups are selected from the groups consisting of hydroxyl, ketone, aldehyde, carboxyl and amine groups. In an especially preferred embodiment, the chemical groups are hydroxyl groups. Alternatively, the preferred embodiment of the present invention is manufactured by selective exposure of a homogeneous polymer containing side chains cleavable by an acid, base, or other physical means such as reactive plasma, laser, and UV radiation. Selective cleavage of hydrophobic side chains in molecules within a defined region will result in hydrophilic surface characteristics. For example, exposure of polyvinyl acetate (PVAc) surface to a strong base such as KOH generates hydroxyl groups and renders the PVAc surface hydrophilic.

In an alternative method, UV light is used to cleave hydrophobic side chains in a porous matrix consisting of a homogeneous, hydrophobic, UV transparent polymer. Cleavage of the side chains will make the UV-exposed region hydrophilic while masked regions remain hydrophobic with side chains intact.

Another method of forming cell adhesive regions utilizes reactive plasma treatment. Plasma is a partially ionized gas containing ions, electrons, atoms, and neutral species. Reactive plasma is highly reactive to the surface of a polymer. For example, oxygen plasma treatment involves using plasma in the presence of oxygen to form peroxides on the surface of the membrane. The peroxides subsequently decompose to form oxygen-containing radical groups. Commonly used gases for the plasma treatment of polymers include oxygen, argon, nitrous oxide, tetrafluoromethane, and air. Oxygen plasma treatment of a hydrophobic polymer surface such as polytetraflouroethylene (PTFE) renders the treated surface hydrophilic.

In another preferred embodiment, the top surface is modified by physical modification to form the cell adhesive and dis-adhesive regions. Physical modifications include preparation of an interpenetrating network (IPN) with a second polymer, and mechanical scratching to provide for the friction necessary for cell adhesion. In a preferred embodiment, the physical modification is generation of an IPN. In this embodiment, a hydrophobic monomer is soaked into a hydrophilic substrate and subsequently polymerized using photolithography. Regions unexposed to the photolithography where the monomer does not polymerize are then washed with solvent, leaving a patterned polymerized hydrophobic region.

Cell dis-adhesive regions are designed to allow for separation of cells which are associated or adhered to the top surface. In other words, providing regions on the top surface wherein the cells cannot associate or adhere allows discrete clusters of cells to separated from each other. A variety of methods may be used to prepare the cell dis-adhesive regions, including methods used to prepare cell adhesive regions. Examples of such methods include hydrophobilization of the top surface to form cell dis-adhesive regions. Methods of hydrophobilization include photochemical modification and laser ablation. In a preferred embodiment the photochemical modification includes regional polymerization and regional formation of an IPN. Each of the methods of preparation of cell dis-adhesive regions is discussed in detail below.

Photolithographic methods are used to selectively define hydrophilic regions on a hydrophobic surface or vice versa. Photolithographic techniques use a template or mask to selectively shield portions of the surface from precipitating polymers formed when a dimer gas such as acetylene ($C_2H_2$), trifluorochloroethylene ($C_2F_3Cl$), or tetrafluoroethylene ($C_2F_4$) is illuminated in a vacuum by a deep ultraviolet light source (250-200 nanometer (nm) wavelength). The ultraviolet light initiates polymerization reactions in the gas and after sufficient chain lengths have been attained, molecules of polymer precipitate onto the surface being treated. This technique is used to selectively make hydrophobic surface regions on a hydrophilic substrate or vice versa. For example, photolithography using tetrafluoroethylene as the reactant dimer gas will result in deposition of hydrophobic polytetraflouroethylene (PTFE) which is used to selectively define hydrophobic regions on a hydrophilic surface such as cellulose or polyacrylnitrile.

Bulk hydrophobic and hydrophilic regions are incorporated into the porous matrix by using the same photolithographic techniques already described, but the UV light is applied to a transparent porous matrix marinated with polymerizable compounds. Exposing such a pretreated matrix to UV light will polymerize the polymerizable compounds contained within, rendering the exposed regions either hydrophobic or hydrophilic depending on the chemical/physical nature of the chosen polymerizable compounds present. Unpolymerized compounds may be washed away from the porous matrix before use or alternatively, unpolymerized compounds may be dialyzed and rendered hydrophilic. In such a way, a second polymer network is formed upon UV exposure, which interpenetrates with the preexisting network of the porous matrix. This configuration is called interpenetrating polymer networks (IPN).

The cell dis-adhesive region (9) of the top surface of the porous block is a region to which cells bind or adhere with a reduced capacity as compared to the cell adhesive region. In a preferred embodiment cells do not measurably bind to the cell dis-adhesive region. The top surface of the porous block may inherently comprise cell dis-adhesive regions or the top surface of the porous block may be modified to form a cell dis-adhesive region.

In certain embodiments the top surface is modified by regional hydrophobilization to form the cell dis-adhesive regions.

Alternatively, a preferred embodiment of the present invention is prepared using laser ablation techniques. Laser ablation in its broadest sense involves the use of high energy light to remove or transform material on a surface. Laser ablation of a polymer results in chemical dissolution of the polymer and therefore is used to transform exposed porous matrix regions from a hydrophobic to a hydrophilic character and vice versa. Laser ablation can also be used to precipitate material with the desired wetting characteristics onto the porous matrix surface. This involves laser radiation impinging on the target containing the material to be transferred, absorption of energy, localized surface heating, and resultant material evaporation. This material forms a plume that is precipitated onto the target porous matrix substrate.

Figure 5:
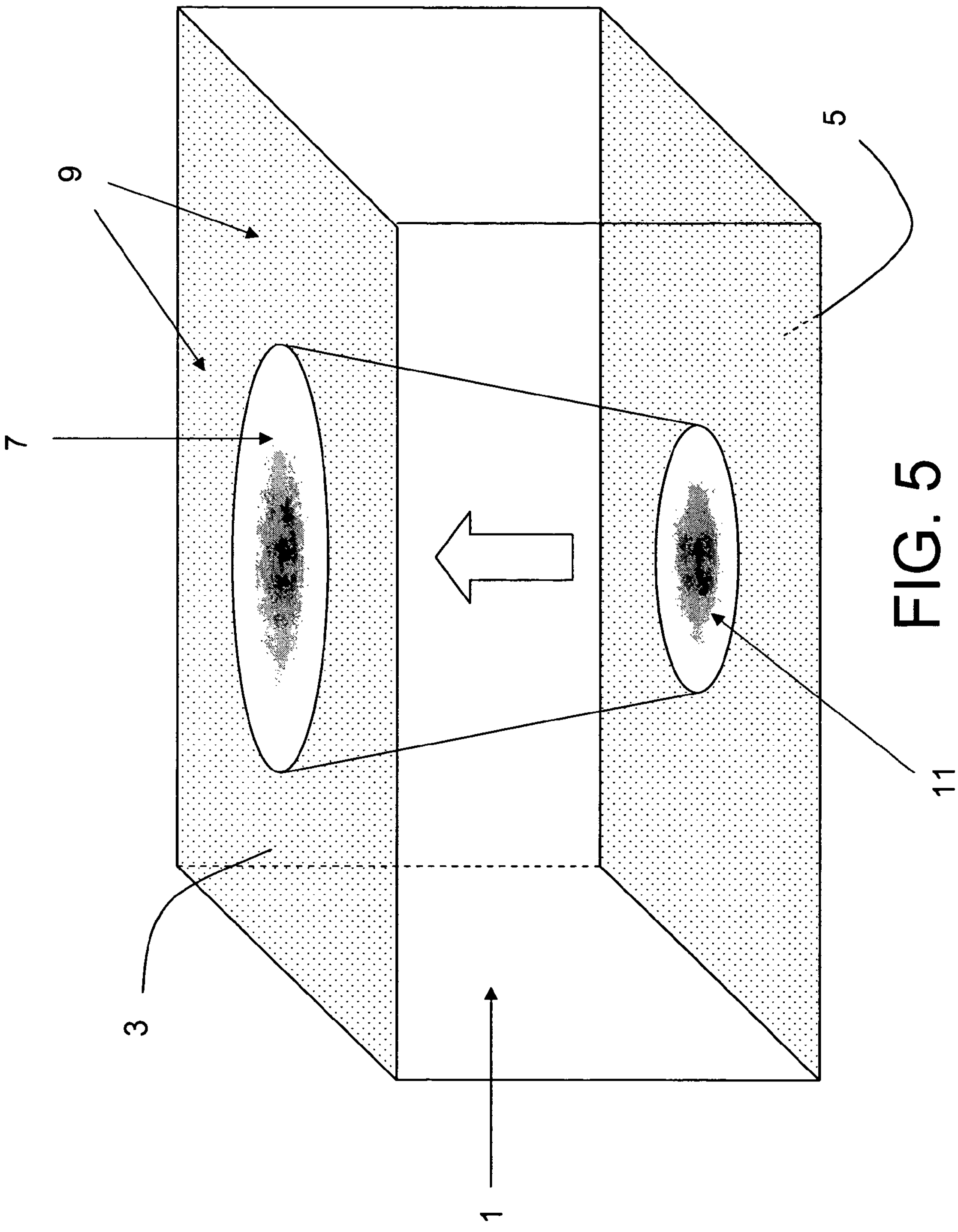
FIG. 5. Schematic showing the diffusion of a sample compound from a single site (11), located on the bottom surface (5) of the apparatus toward a single hydrophilic cell adhesive region (7) located on the top surface (3) of the apparatus.

Referring to FIG. 1, the compounds are loaded onto multiple sites (11), windows, or wells on the bottom surface (5) of the porous block (1). The compounds are loaded onto the sites (11) and absorbed into the block by capillary attraction of the porous material (see FIG. 5). In a preferred embodiment, there are thousands of small sites (11), windows, or wells on the bottom surface (5) of the porous block (1). These sites are located opposite from the cell adhesive regions (7) on the top surface (3) of the porous block (1).

In an embodiment of the present invention, hydrophilic regions on the top surface of the porous matrix layer are vertically aligned with geometrically identical hydrophilic regions arrayed on the bottom surface of the porous matrix layer. Hydrophilic regions on the top surface aid in the preparation of surface characteristics that are attractive to assay components. Hydrophilic regions on the bottom surface aid in localizing sample compounds and their carrier solvent deposited onto the porous matrix layer using a micropipette or automated micro-fluid handling technologies. Alignment of top and bottom surface regions optimizes the interaction of sample compounds placed on the bottom surface which then diffuse through the porous layer to the assay components (e.g., cells) fixed to the top surface by ensuring that assay components are exposed to the maximum sample dose corresponding to the central axis of the diffusion cone.

In another embodiment of the present invention, circular hydrophilic regions on the top surface of the porous matrix layer are vertically aligned with geometrically identical hydrophobic regions arrayed on the bottom surface of the porous matrix layer. As in the previous embodiment, hydrophilic regions on the top surface aid in the preparation of surface characteristics that are attractive to assay components or function to fix assay components such as cells within these predetermined areas. Hydrophobic regions on the bottom surface of the porous block aid in localizing sample compounds carried in a solvent deposited onto the surface using a micropipette or automated micro-fluid handling technologies. This top and bottom surface region alignment optimizes sample and assay component interaction.

Any type of cell can be used with the present application. The cells may be immortalized or primary cells. In certain embodiments the cells have been transfected with a gene of interest.

In preferred embodiments the cells are adherent cells. In another preferred embodiment the cells are eukaryotic cells. In a particularly preferred embodiment the cells are mammalian cells. In an especially preferred embodiment the cells are human cells.

Examples of cells that are utilized with the present invention include, but are not limited to, BHK, C2C12, CHO, COS-1, COS-7, F9, HEK293, HeLa, Jurkat, L8, L929, NIH3T3, PC-12, Sf9 cells.

It should be recognized that one of skill in the art would also be able to modify the present invention to determine the interaction of non-cellular material with the sample compounds. For example, instead of plating cells onto the cell adhesive regions of the top surface, peptides and other chemical compounds can also be adhered to the cell adhesive region and tested for interaction with sample compounds.

Figure 2:
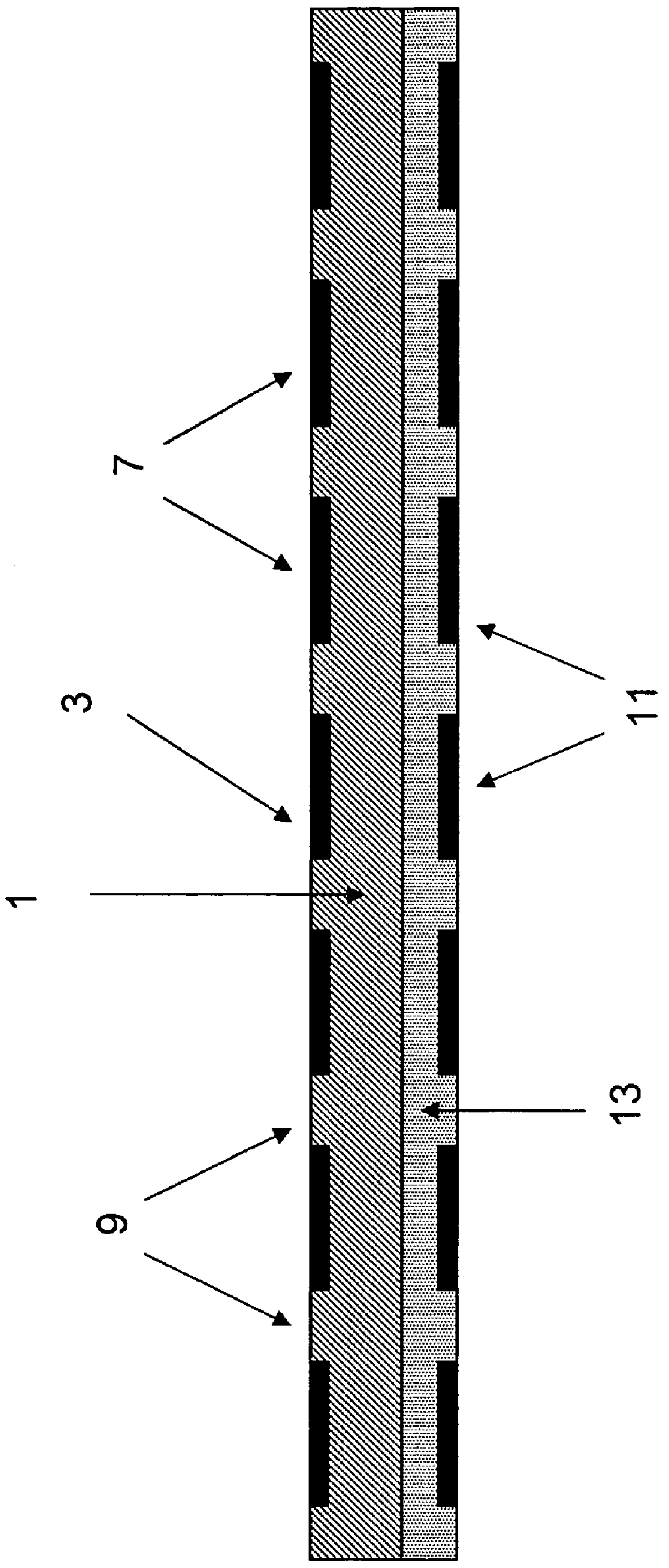
FIG. 2. Cross sectional view of apparatus with dissolvable layer (13).

Referring to FIG. 2, the apparatus may include a dissolvable layer (13) which provides multiple sites to load the sample compounds. These sites are located opposite from the cell adhesive regions on the top surface (3) of the porous block (1).

The purpose of the dissolvable layer is to control the diffusion of drugs through the layer. In a preferred embodiment, the dissolvable layer dissolves about 1 to about 2 hours after the cells are placed onto the plate to ensure immobilization of cells on the plate.

The dissolvable layer may be temperature-sensitive, humidity-sensitive, pH-sensitive, or sensitive to specific chemicals (for example, ions, glucose, or urea). In certain embodiments the dissolvable layer is agarose, gelatin, chitin, polyacrilic acid, and poly(N-isopropyl acrylamide) or Pluronic™ (α-Hydro-ω-hydroxypoly(oxyethylene)poly(oxypropylene)poly(oxyethylene) block copolymer).

Figure 3:
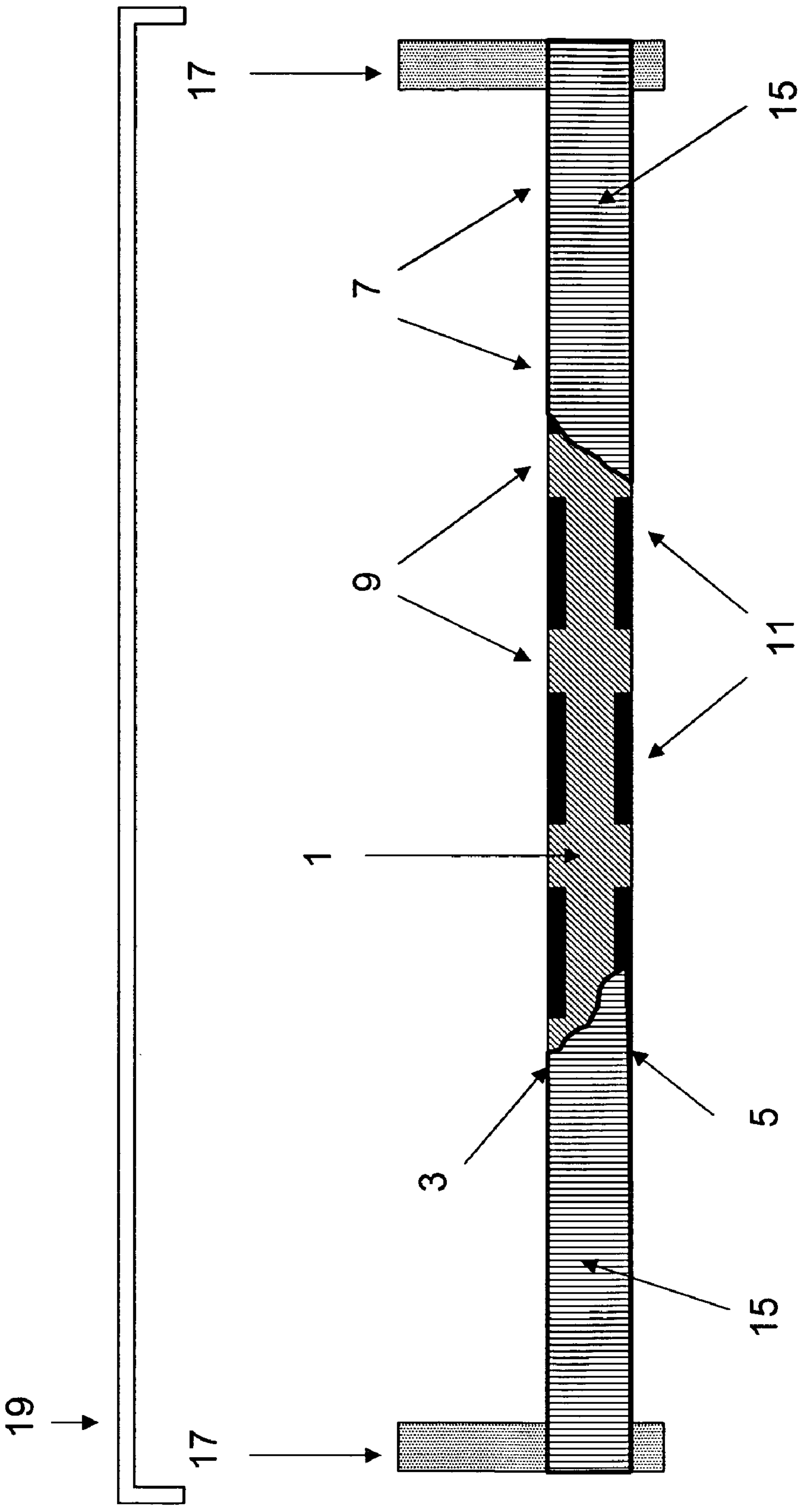
FIG. 3. Cross sectional view of apparatus with frame (15) and wall (17) extending from frame.
Figure 4:
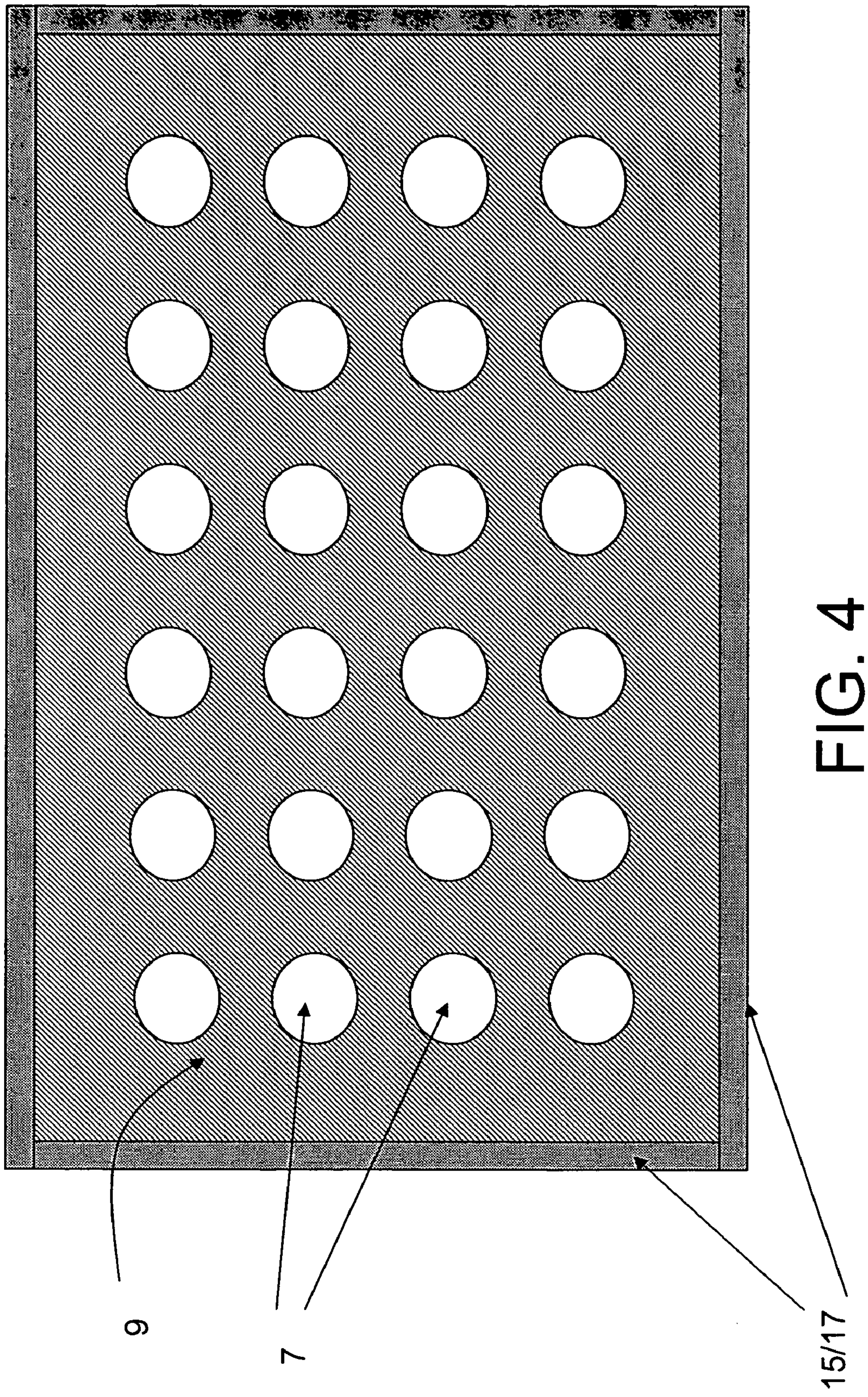
FIG. 4. Top view of apparatus with frame (15) showing hydrophilic cell adhesive regions (7) and hydrophobic cell dis-adhesive regions (9).

Referring to FIGS. 3 and 4 (FIG. 3 is a cross-sectional view of FIG. 4), in a preferred embodiment, the apparatus further comprises a frame (15) surrounding the porous block. The frame provides structural support such that the porous block is maintained in a substantially planar position during various manipulations.

In another embodiment the apparatus further comprises a retaining wall (17) surrounding the entire top surface of the porous matrix block. The wall allows an assay reagent suspension to be dispensed onto the surface and maintained in contact with the top surface while cellular, protein or other biological components interact with the defined cell adhesive regions of the top surface. When the suspension is decanted and the surface optionally rinsed, the cellular, protein or other biological components are maintained and fixed within the defined cell adhesive regions. Sample compounds diffusing through the porous matrix layer can now interact with these cellular, protein or other biological components on the top of the porous block. In certain embodiments the porous block comprises the wall. In another embodiment the frame comprises the wall.

In another embodiment the top and/or bottom surfaces of the apparatus are covered with a lid (19) or film. The lid (19) or film prohibits the incubated cells or loaded compounds from contamination and keeps the apparatus sterile.

Compounds according to the present invention as used herein in the context of a "sample compound", "test compound", or a "drug candidate compound" described in connection with the apparatus of the present invention. As such, these compounds comprise organic or inorganic compounds, derived synthetically or from natural sources.

The advent of combinatorial chemistry has driven advances in high-throughput screening methods designed to identify potentially promising drug candidates. Combinatorial chemistry relies on automated processes to create large populations of potential drug leads systematically and efficiently.

For example, it is desirable to be able to screen large numbers of naturally occurring compounds such as those used in nontraditional medicine. In addition, it is desirable to be able to screen large numbers of known pre-existing drugs and compounds for biological activity beyond their currently known activity. Also, it is desirable to be able to screen large numbers of nucleic acids and nucleic acid analogs, including sense and antisense oligonucleotides, RNAi, siRNAs, plasmids, and thiophosphate oligonucleotides.

Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, antibodies including, without limitation, poly- and monoclonal antibodies, antibody fragments (for example, FAb fragments and $F(ab)_2$ fragments), single-chain antibodies, anti-idiotypic antibodies, and chimeric or humanized versions of such antibodies or fragments, as well as human antibodies and antibody fragments. The assays are performed in a variety of formats, including protein-protein binding assays, biochemical screening assays, immunoassays and cell based assays, which are well characterized in the art.

The mixture components are added in any order that provides for the requisite activity. Incubation may be performed at any temperature that facilitates optimal binding, typically between about 4° C. and 40° C., more commonly between about 30° C. and 40° C. Incubation periods are likewise selected for optimal binding but also minimized to facilitate rapid, high-throughput screening, and are typically between about 0.1 and 48 hours, preferably between 12 and 36 hours, more preferably between 20 and 24 hours. After incubation, the effect of the candidate compound is determined using a convenient assay. Such assays include, but are not limited to, assays which measure changes in cell appearance or structure, changes in cell activity, changes in gene expression levels, changes in cell protein expression levels, changes in cell protein activity, and changes in cell protein stability.

Suitable compounds that bind to the cells include polypeptide or polynucleotide fragments or small molecules, e.g., peptidomimetics. Small molecule compounds, which are usually less than 100 kD molecular weight, and more preferably less than 10 kD, are preferable as therapeutics since they are more likely to be permeable to cells, are less susceptible to degradation by various cellular mechanisms, and are not as likely to elicit an immune response as would proteins or polypeptides. Small molecules include but are not limited to synthetic organic or inorganic compounds. Large molecule compounds (compounds greater than 100 kD) can also be utilized. Many pharmaceutical companies have extensive libraries of such molecules, which are conveniently screened by using the assays of the present invention. Non-limiting examples include proteins, peptides, glycoproteins, glycopeptides, glycolipids, polysaccharides, oligosacchardies, nucleic acids, bioorganic molecules, peptidomimetics, pharmacological agents and their metabolites, transcriptional and translation control sequences.

A technique for identifying compounds that interact with the cells may utilize a chimeric substrate (e.g., epitope-tagged fused or fused immunoadhesin). The binding of the candidate molecules, which are optionally labeled (e.g., radiolabeled), to the cell is measured.

In an embodiment of the present invention, samples are delivered and diffused through the porous block after cells have adhered. The samples interact with the cells and the resultant biological effect indicates the potential pharmaceutical efficacy of a sample compound. The apparati of the present invention demonstrate highly predictable and reproducible responses to known compounds or other control conditions, and demonstrate a clear threshold between positive and negative responses. The invention also demonstrates suitability and reproducibility of an assay for high-throughput screening (HTS) using a diverse collection of at least a few hundred compounds, such as a collection of FDA approved drugs or other bioactive molecules. Certain embodiments of the invention require the availability of reagents necessary to perform HTS, such as enzyme indicators, chemicals necessary for reagent readout, and capacity to generate sufficient reaction substrates (DNA, RNA, protein, or enzyme substrates). Those of skill in the art may utilize a variety of known methods for evaluating the significance of the samples which demonstrate pharmacological activity in a primary high throughput screen. These methods can be used for the evaluation of multiple hit compounds that may be identified in a primary HTS effort. Secondary screens may also be used to rule out artifacts and appropriate counterscreens may be included in order to prioritize compounds for further testing.

Biological effects include effects measured by monitoring cell number, configuration, size, adhesion, morphology, or death through microscopic observation.

In addition to microscopic observation, biological effects can be measured using assays. The assays measure the ability of candidate compounds to induce cell metabolic activity, cell adhesion, cell proliferation, cell growth or cell death (necrosis or apoptosis). These assays include the MTT (3-(4,5-dimethylthiazol-2-yl)-2,5-diphenyl tetrasodium bromide) assay, caspase assays, Cr51-release assays, ATP assays, fragmented DNA assays, and other known methods of measuring cell death.

The assays also include monitoring or tracking specific molecule markers, such as reporters of gene expression, reporters of enzyme activity, or cell signaling molecules.

As discussed above, the porous block comprises a top surface which comprises a plurality of cell adhesive regions and cell dis-adhesive regions. These regions can extend from the top surface to the bottom surface or extend from the top surface to some point in between the top surface and bottom surface. In a preferred embodiment, hydrophilic regions are aligned on both top and bottom surfaces and contiguous through the entire porous matrix layer. Hydrophilic top and bottom regions aid, as in previous embodiments, in fixing assay reagents and localizing sample deposition. The extension of these hydrophilic regions through the porous matrix facilitates diffusion by retaining the sample compound within the hydrophilic region, thereby maximizing the yield of sample compound at the top surface, and minimizing the degree of sample to sample contamination arising from significant lateral diffusion of sample compounds through the porous matrix. This embodiment is discontinuous both within the porous matrix and at its surfaces.

EXAMPLES

Example 1

Formation of Porous Block

The porous block is made of hydrophilic porous nylon membrane of 10 mm in diameter and approximately 100 micron in thickness, with typical pore size of 0.45 microns. The membrane is then soaked in monomeric methyl methacrylate (MMA). The nylon membrane is then sandwiched between two glass plates under sterile conditions.

Example 2

Formation of Cell Adhesive Regions

To generate cell adhesive regions, the MMA-soaked nylon membrane is exposed to a laser beam with diameter of 300 microns to selectively heat the membrane to 70° C. at specific regions for 5 seconds. MMA in these selectively heated regions will polymerize and form hydrophobic regions, while the area of the MMA-soaked nylon membrane unexposed to the laser beam stays intact and remains hydrophilic. In this way a porous block is generated that comprises 96 hydrophilic cell-adhesive regions. The membrane is then removed from the glass plates and washed with ethanol to remove excess MMA. A hydrophilic nylon membrane with patterned hydrophobic region is then formed.

The patterned membrane is then removed from the mold and inserted into a frame comprising walls. The frame provides additional support for the porous block, while the walls allow liquid containment.

Example 3

Plating of Cells

NIH3T3 fibroblasts are plated onto the porous block in DMEM medium supplemented with 10% calf serum at a density of 1-10×$10^4$ cells/ml and incubated in a 5% $CO_2$ incubator at 37° C. overnight.

The next day the medium is changed.

Example 4

Loading of Sample Compounds

A library of various compounds is obtained from synthesis or chemical isolation and purification. These compounds are dissolved in sterile PBS and applied to the bottom surface of the porous block at 96 different sites which are directly opposite from the cell adhesive regions using a liquid transferring machine or arrayer. The porous block can be turned upside down (i.e., the bottom surface on top) to facilitate loading. The porous block is then returned to the incubator for at least 6 hours.

Example 5

MTT Assay

The cells are washed three times with PBS. Then a 5 mg/ml MTT solution is added (at a DMEM media: MTT solution ratio of 5:1) to the plate containing cells followed by incubation of the plate and cells in a $CO_2$ incubator at 37° C. for 5 hours. The media is then removed with a needle and syringe. At this point DMSO is added (at a DMEM media: MTT solution ratio of 2:1) to each well. It may be necessary to pipette up and down to dissolve any crystals. The plate is then incubated at 37° C. for 5 minutes and transferred to a plate reader and absorbance measured at 550 nm.

We claim:

1. An apparatus for testing multiple sample compounds for their biological effect comprising a porous block having substantially planar top and bottom surfaces, said top surface comprising a plurality of cell adhesive regions and cell dis-adhesive regions, said bottom surface providing multiple sites to load said sample compounds, said sites located opposite from said cell adhesive regions on said top surface of said porous block;

wherein when sample compounds are loaded to the sites, they diffuse through the porous block to the oppositely positioned cell adhesive regions.

2. An apparatus for testing multiple sample compounds for their biological effect comprising:

(a) a porous block having substantially planar top and bottom surfaces, said top surface comprising a plurality of cell adhesive regions and cell dis-adhesive regions; and (b) at least one dissolvable layer which provides multiple sites to load said sample compounds, said sites located opposite from said cell adhesive regions on said top surface of said porous block, wherein said dissolvable layer is adjacent to said bottom surface and the dissolvable layer controls the diffusion of the said sample compounds through the porous block.

3. The apparatus of claim 1 wherein said apparatus further comprises a frame surrounding said porous block.

4. The apparatus of claim 1 wherein said apparatus further comprises a wall that rises above and surrounds said top surface, wherein the combination of said wall and said top surface is capable of retaining a liquid.

5. The apparatus of claim 1 wherein said top surface is modified to form said cell adhesive regions.

6. The apparatus of claim 1 wherein said porous block is permeable to compounds having a molecular weight less than 100 kDa.

7. The apparatus of claim 1 wherein said porous block comprises a polymer.

8. The apparatus of claim 7 wherein said polymer is selected from the group consisting of polyamide (nylon), polycarbonate, EVAc, PET, and polysulfone.

9. The apparatus of claim 1 wherein said porous block comprises a gel.

10. The apparatus of claim 9 wherein said gel is selected from the group consisting of agarose, gelatin, αHydro-ω-hydroxypoly(oxyethylene)poly(oxypropylene) poly (oxyethylene) block copolymer, stimuli sensitive hydrogel, and modified starch/cellulose.

11. The apparatus of claim 10 wherein said stimuli sensitive hydrogel is selected from the group consisting of poly(n-isopropylarylamide) and polyacrylic acid.

12. The apparatus of claim 1 wherein said porous block comprises a membrane.

13. The apparatus of claim 12 wherein said membrane is selected from the group consisting of nylon, cellulose, EVAc, PET, and polysulfone.

14. The apparatus of claim 6 wherein said cell adhesive regions extend from said top surface to said bottom surface.

15. The apparatus of claim 6 wherein said top surface is modified by regional hydrophilization to form said cell adhesive regions.

16. The apparatus of claim 1 wherein said top surface is modified to form said cell dis-adhesive regions.

17. The apparatus of claim 16 wherein said top surface is modified by regional hydrophobization to form said cell dis-adhesive regions.

18. The apparatus of claim 6 wherein said top surface is modified by regional addition of at least one peptide to form said cell adhesive regions.

19. The apparatus of claim 18 wherein said at least one peptide is selected from the group consisting of RGD and polylysine.

20. The apparatus of claim 6 wherein said top surface is modified by regional saccharification to form said cell adhesive regions.

21. The apparatus of claim 6 wherein said top surface is modified by regional protein modification or absorption to form said cell adhesive regions.

22. The apparatus of claim 21 wherein said regional protein modification comprises modification at least one protein selected from the group consisting of fibronectin and collagen.

23. The apparatus of claim 6 wherein said top surface is modified by chemical groups to form said cell adhesive regions.

24. The apparatus of claim 23 wherein said chemical groups are selected from the groups consisting of hydroxyl, ketone, aldehyde, carboxyl and amine groups.

25. The apparatus of claim 6 wherein said top surface is modified by physical modification to form said cell adhesive regions.

26. The apparatus of claim 25 wherein said physical modification is a method selected from the group consisting of mechanical scratch, chemical corrosion, or laser ablation.

27. The apparatus of claim 1 wherein said cell adhesive regions and said cell dis-adhesive regions are prepared by a process selected from the group consisting of photolithography, regional polymerization, and regional formation of an interpenetrating network.

28. The apparatus of claim 1 wherein said multiple samples are loaded on said multiple sites.

29. The apparatus of claim 1 wherein said multiple sites are hydrophilic dots or wells.

30. The apparatus of claim 1 wherein said multiple sites are hydrophobic dots or wells.

31. The apparatus of claim 2 wherein said dissolvable layer comprises polymers that are temperature, humidity, or pH sensitive.

32. The apparatus of claim 2 wherein said dissolvable layer comprises degradable polymers.

33. The apparatus of claim 2 wherein said dissolvable layer is impermeable to said sample compounds.

34. The apparatus of claim 2 wherein said dissolvable layer allows diffusion of said sample compounds after dissolution of said dissolvable layer.

35. The apparatus of claim 2 wherein said dissolvable layer has a diffusion coefficient that differs between its dissolved state and un-dissolved state.

36. The apparatus of claim 31 wherein said polymers are selected from the group consisting of agarose, gelatin, chitin, polyacrilic acid, and poly(N-isopropyl acrylamide).

37. The apparatus of claim 32 wherein said degradable polymers comprises α-Hydro-ω-hydroxypoly(oxyethylene) poly(oxypropylene)poly(oxyethylene) block copolymer.

38. The apparatus of claim 6 wherein said top surface is modified by regional hydrophobization to form said cell adhesive regions.

39. The apparatus of claim 16 wherein said top surface is modified by regional hydrophilization to form said cell dis-adhesive regions.

* * * * *

SEQUENCE LISTING

<160> NUMBER OF SEQ ID NOS: 4

<210> SEQ ID NO 1
<211> LENGTH: 3
<212> TYPE: PRT
<213> ORGANISM: Artificial
<220> FEATURE:
<223> OTHER INFORMATION: adhesion ligand for members of the integrin family

<400> SEQUENCE: 1

Arg Gly Asp
1

<210> SEQ ID NO 2
<211> LENGTH: 6
<212> TYPE: PRT
<213> ORGANISM: Artificial
<220> FEATURE:
<223> OTHER INFORMATION: adhesion ligand for members of the integrin family

<400> SEQUENCE: 2

Gly Arg Gly Asp Ser Pro
1 5

<210> SEQ ID NO 3
<211> LENGTH: 5
<212> TYPE: PRT
<213> ORGANISM: Artificial
<220> FEATURE:
<223> OTHER INFORMATION: adhesion ligand for members of the integrin family; Phe is a D-amino acid

<400> SEQUENCE: 3

Arg Gly Asp Phe Val
1 5

<210> SEQ ID NO 4
<211> LENGTH: 5
<212> TYPE: PRT
<213> ORGANISM: Artificial
<220> FEATURE:
<223> OTHER INFORMATION: activation site immediately adjacent to the transmembrane domain of the alpha integrin chain

<400> SEQUENCE: 4

Gly Phe Phe Lys Arg
1 5